(12) United States Patent
Ueda et al.

(10) Patent No.: US 9,978,963 B2
(45) Date of Patent: May 22, 2018

(54) MATERIAL FOR ORGANIC ELECTROLUMINESCENT ELEMENTS, AND ORGANIC ELECTROLUMINESCENT ELEMENT USING SAME

(71) Applicant: NIPPON STEEL & SUMIKIN CHEMICAL CO., LTD., Tokyo (JP)

(72) Inventors: Tokiko Ueda, Kitakyushu (JP); Junya Ogawa, Kitakyushu (JP); Takahiro Kai, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 90 days.

(21) Appl. No.: 15/023,797

(22) PCT Filed: Aug. 28, 2014

(86) PCT No.: PCT/JP2014/072534
§ 371 (c)(1),
(2) Date: Mar. 22, 2016

(87) PCT Pub. No.: WO2015/045718
PCT Pub. Date: Apr. 2, 2015

(65) Prior Publication Data
US 2016/0218304 A1 Jul. 28, 2016

(30) Foreign Application Priority Data

Sep. 30, 2013 (JP) .................. 2013-204374

(51) Int. Cl.
| | | |
|---|---|---|
| H01L 51/00 | (2006.01) | |
| C07F 7/08 | (2006.01) | |
| H01L 51/50 | (2006.01) | |

(52) U.S. Cl.
CPC .......... *H01L 51/0094* (2013.01); *C07F 7/082* (2013.01); *C07F 7/0814* (2013.01);
(Continued)

(58) Field of Classification Search
CPC ..................... C07F 5/027; C07F 7/08–7/0898
See application file for complete search history.

(56) References Cited

U.S. PATENT DOCUMENTS

| | | | |
|---|---|---|---|
| 2012/0319088 A1 | 12/2012 | Lee et al. | |
| 2014/0332792 A1* | 11/2014 | Tada | .................. H01L 51/0067 257/40 |

FOREIGN PATENT DOCUMENTS

| | | | |
|---|---|---|---|
| JP | 2003-515897 A | 5/2003 | |
| JP | 2005-162709 A | 6/2005 | |

(Continued)

OTHER PUBLICATIONS

Machine-generated English translation of WO 2014/103724 A1.*
(Continued)

*Primary Examiner* — Vu A Nguyen
(74) *Attorney, Agent, or Firm* — Locke Lord LLP

(57) ABSTRACT

Provided are an organic electroluminescent device (organic EL device) that is improved in luminous efficacy, sufficiently secures driving stability, and has a simple construction, and a material for organic EL devices to be used in the organic EL device. The material for organic EL devices is a material for organic EL devices formed of an ortho-carborane compound having a structure in which a silyl group (—SiR$_3$) is bonded to a divalent ortho-carborane group represented by $C_2B_{10}H_{10}$ through an aromatic group. In addition, the organic electroluminescent device is an organic electroluminescent device having a structure in which an anode, an organic layer, and a cathode are laminated on a substrate, the device having an organic layer containing the ortho-carborane compound, and the organic layer being a light-emitting layer, an electron-transporting layer, a hole-blocking layer, or an exciton-blocking layer.

7 Claims, 2 Drawing Sheets

(52) U.S. Cl.
CPC ...... *H01L 51/0052* (2013.01); *H01L 51/0058* (2013.01); *H01L 51/0067* (2013.01); *H01L 51/0072* (2013.01); *H01L 51/0079* (2013.01); *H01L 51/5096* (2013.01)

(56) References Cited

FOREIGN PATENT DOCUMENTS

| JP | 2005-166574 A | 6/2005 | | |
|---|---|---|---|---|
| WO | WO-2013/088934 A1 | 6/2013 | | |
| WO | WO-2013/094834 A1 | 6/2013 | | |
| WO | WO-2014/103724 A1 | 7/2014 | | |
| WO | WO 2014103724 A1 | * | 7/2014 | ......... H01L 51/0058 |

OTHER PUBLICATIONS

Kyung-Ryang Wee et al., "Carborane-Based Optoelectronically Active Organic Molecules: Wide Band Gap Host Materials for Blue Phosphorescence," J. Am. Chem. Soc. 2012, 134, pp. 17982-17990.
Yu-Man Wang et al., "Synthesis, characterization, and reactions of 6,13-disubstituted 2,3,9,10-tetrakis(trimethylsilyl)pentacene derivatives," Tetrahedron, 2007, vol. 63, pp. 8586-8597.
Chang Hwan Shin et al., "Group 4 *ansa*-metallocenes derived from o-carborane and their luminescent properties," Journal of Organometallic Chemistry, 2009, vol. 694, pp. 1623-1631.
International Search Report dated Oct. 21, 2014, issued for PCT/JP2014/072534.
International Search Report and Written Opinion dated Oct. 21, 2014, issued for PCT/JP2014/072534.

* cited by examiner

MATERIAL FOR ORGANIC ELECTROLUMINESCENT ELEMENTS, AND ORGANIC ELECTROLUMINESCENT ELEMENT USING SAME

TECHNICAL FIELD

The present invention relates to an organic electroluminescent device using an ortho-carborane compound as a material for organic electroluminescent devices, and more specifically, to a thin film-type device that emits light by applying an electric field to a light-emitting layer containing an organic compound.

BACKGROUND ART

In general, an organic electroluminescent device (hereinafter referred to as organic EL device) includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficacy particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex ($Alq_3$) are formed between electrodes as thin films, resulting in a significant improvement in luminous efficacy, as compared to related-art devices in which a single crystal of anthracene or the like is used. Thus, the development of the above-mentioned organic EL device has been promoted in order to accomplish its practical application to a high-performance flat panel having features such as self-luminescence and rapid response.

Further, investigations have been made on using phosphorescent light rather than fluorescent light as an attempt to raise the luminous efficacy of a device. Many kinds of devices including the above-mentioned device in which a hole-transporting layer formed of an aromatic diamine and a light-emitting layer formed of $Alq_3$ are formed emit light by using fluorescent light emission. However, by using phosphorescent light emission, that is, by using light emission from a triplet excited state, luminous efficacy is expected to be improved by from about three times to about four times, as compared to the case of using related-art devices in which fluorescent light (singlet) is used. In order to accomplish this purpose, investigations have been made on adopting a coumarin derivative or a benzophenone derivative as a light-emitting layer, but extremely low luminance has only been provided. Further, investigations have been made on using a europium complex as an attempt to use a triplet state, but highly efficient light emission has not been accomplished. In recent years, many investigations have been made mainly on an organic metal complex, such as an iridium complex, as described in Patent Literature 1, for the purpose of attaining high luminous efficacy and a long lifetime.

A device construction is also important for obtaining high luminous efficacy. For example, the following construction is given. A hole-blocking layer is laminated between the light-emitting layer and an electron-transporting layer for the purpose of trapping a hole in the light-emitting layer to increase the probability that an electron and the hole recombine in the light-emitting layer. The use of the hole-blocking layer can be expected to improve the luminous efficacy.

As described in the foregoing, both charges (a hole and an electron) need to recombine in the light-emitting layer with high probability in order that high luminous efficacy may be obtained in the organic EL device. Further, hole-blocking materials (including an electron-transporting material) themselves have been desired to be compounds each of which is electrochemically stable, and brings together high heat resistance and excellent amorphous stability, and hence further improvements thereof have been required.

CITATION LIST

Patent Literature

[PTL 1] JP 2003-515897 A
[PTL 2] JP 2005-162709 A
[PTL 3] JP 2005-166574 A
[PTL 4] US 2012/0319088 A1
[PTL 5] WO 2013/094834 A1

Non Patent Literature

[NPL 1] J. Am. Chem. Soc. 2012, 134, 17982-17990

In Patent Literatures 2 to 5 and Non Patent Literature 1, there are disclosures of such carborane compounds as shown below.

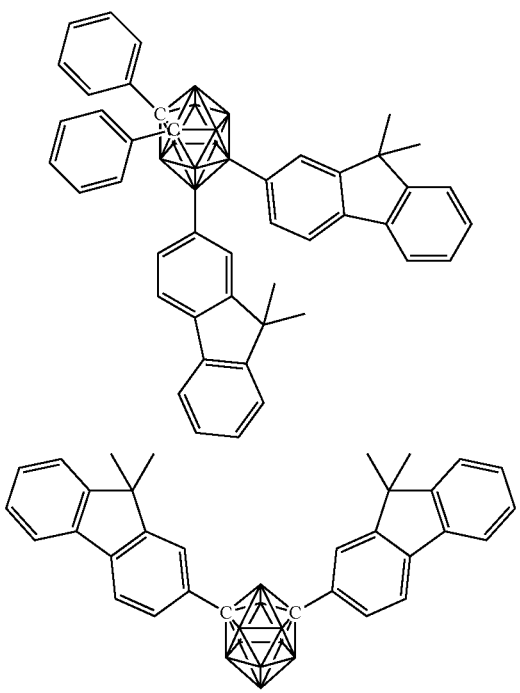

-continued

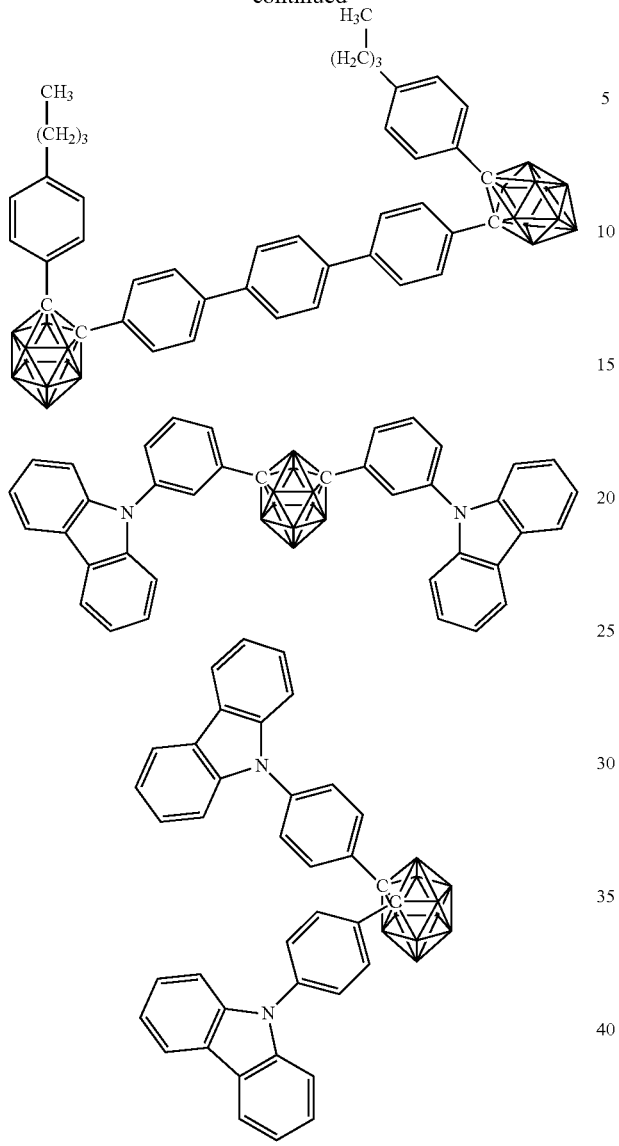

However, none of the literatures discloses the usefulness of a compound obtained by bonding a silyl group to a carbon atom of an ortho-carborane skeleton through an aromatic group.

SUMMARY OF INVENTION

In order to apply an organic EL device to a display device in a flat panel display or the like, it is necessary to improve the luminous efficacy of the device and also to ensure sufficiently the stability in driving the device. The present invention has an object to provide, in view of the above-mentioned circumstances, an organic EL device that has high efficiency and high driving stability and is practically useful and a compound suitable for the organic EL device.

The inventors of the present invention have made intensive investigations and have consequently found that, when an ortho-carborane compound in which a silyl group is bonded through an aromatic hydrocarbon group or an aromatic heterocyclic group is used in an organic EL device, the organic EL device exhibits excellent characteristics. As a result, the present invention has been completed.

The present invention is directed to a material for organic electroluminescent devices, including an ortho-carborane compound represented by the general formula (1).

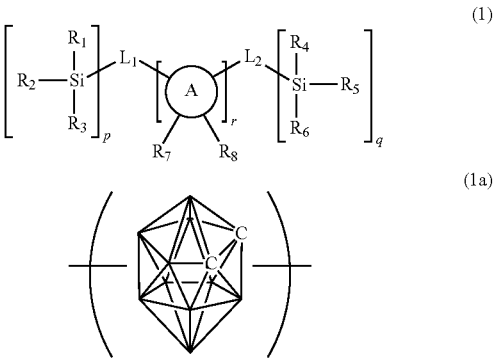

In the general formula (1), a ring A represents a divalent ortho-carborane group $C_2B_{10}H_{10}$ represented by the formula (1a), $L_1$ and $L_2$, which represent a p+1-valent group and a q+1-valent group, respectively, each independently represent a substituted or unsubstituted aromatic hydrocarbon group having 6 to 30 carbon atoms, a substituted or unsubstituted aromatic heterocyclic group having 3 to 30 carbon atoms, or a linked aromatic group formed by linking 2 to 6 aromatic groups selected from the aromatic hydrocarbon group and the aromatic heterocyclic group, when $L_1$ or $L_2$ represents the linked aromatic group, the group may be linear or branched, and the aromatic rings to be linked may be identical to or different from each other, $R_1$, $R_2$, $R_3$, $R_4$, $R_5$, and $R_6$ each independently represent an aliphatic hydrocarbon group having 1 to 12 carbon atoms, a substituted or unsubstituted aromatic hydrocarbon group having 6 to 18 carbon atoms, or a substituted or unsubstituted aromatic heterocyclic group having 3 to 17 carbon atoms, $R_7$ and $R_8$ each independently represent hydrogen, an aliphatic hydrocarbon group having 1 to 12 carbon atoms, a substituted or unsubstituted aromatic hydrocarbon group having 6 to 18 carbon atoms, or a substituted or unsubstituted aromatic heterocyclic group having 3 to 17 carbon atoms, p represents an integer of from 1 to 5, q represents an integer of from 0 to 5, and r represents an integer of from 1 to 4.

Of the ortho-carborane compounds each represented by the general formula (1), an ortho-carborane compound represented by the following general formula (2) is given as a preferred compound.

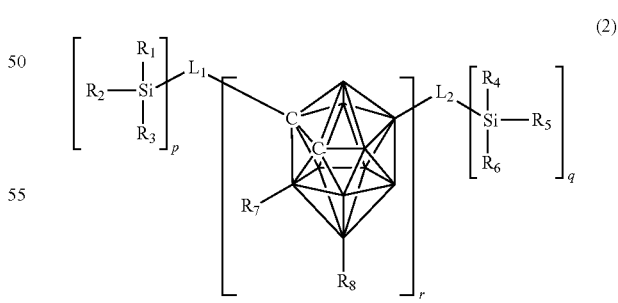

In the general formula (2), $L_1$, $L_2$, $R_1$ to $R_8$, and p to r are identical in meaning to those in the general formula (1).

In the general formula (2), it is preferred that $L_1$ and $L_2$ each independently represent a substituted or unsubstituted aromatic hydrocarbon group having 6 to 18 carbon atoms, a substituted or unsubstituted aromatic heterocyclic group having 3 to 17 carbon atoms, or a linked aromatic group formed by linking 2 to 6 aromatic groups selected from the aromatic hydrocarbon group and the aromatic heterocycle. In addition, it is preferred that $R_1$ to $R_6$ each independently represent an aliphatic hydrocarbon group having 1 to 10 carbon atoms, or a substituted or unsubstituted aromatic hydrocarbon group having 6 to 12 carbon atoms.

The present invention is also directed to an organic electroluminescent device having a structure in which an anode, an organic layer, and a cathode are laminated on a substrate, in which the organic layer includes an organic layer containing the above-mentioned material for organic electroluminescent devices.

Here, the organic layer containing the material for organic electroluminescent devices is preferably an electron-transporting layer, a hole-blocking layer, or an exciton-blocking layer.

The ortho-carborane compound to be used in the organic electroluminescent device of the present invention is also referred to as "material for organic electroluminescent devices" because the compound is used as a material for organic electroluminescent devices. The organic electroluminescent device, which may be a phosphorescent light-emitting device or may be a fluorescent light-emitting device, is preferably a phosphorescent light-emitting device. The ortho-carborane compound has a structure in which a silyl group is bonded to an ortho-carborane skeleton through an aromatic hydrocarbon group or an aromatic heterocyclic group. The ortho-carborane skeleton having bonded thereto to the aromatic hydrocarbon group or the aromatic heterocyclic group has high abilities to inject and transport both charges, but its charge-injecting/transporting properties need to be optimized for additional improvements in characteristics of charge-injecting/transporting. However, it is difficult to control the distribution of a molecular orbital deeply involved in the charge-injecting/transporting properties merely by introducing any other substituent into the aromatic hydrocarbon group or the aromatic heterocyclic group. In view of the foregoing, the inventors have found that the injecting/transporting properties for both charges, especially electron-injecting/transporting properties can be controlled to more preferred ranges by introducing a substituent containing a silicon atom that can divide the spread of the molecular orbital. The use of such compound as a host material having electron-transporting property for a light-emitting layer, a material for the electron-transporting layer, a material for the hole-blocking layer, or a material for the exciton-blocking layer, in the organic EL device can reduce the voltage at which the device is driven.

In addition, the material for phosphorescent devices shows a satisfactory amorphous characteristic and high heat stability because groups linked onto a silicon atom are not present on the same plane, and hence the groups hardly pack or interact with each other, and the crystallinity of the material is low. In other words, a device using the material for phosphorescent devices has enabled the realization of an organic EL device having a long driving lifetime and high durability.

Figure 1:
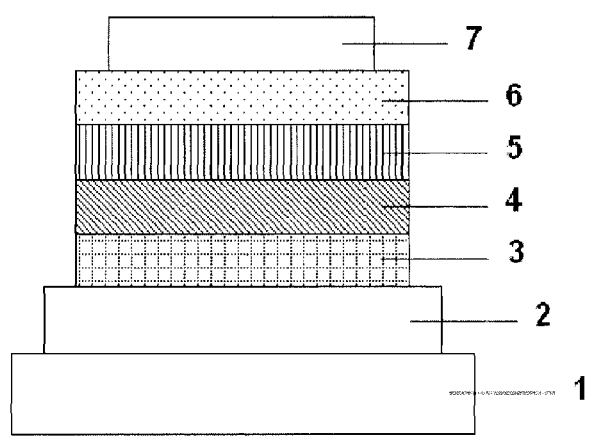
FIG. 1 is a sectional view for illustrating an example of the structure of an organic EL device.

It should be noted that respective reference numerals in FIG. 1 represent the following: 1: a substrate, 2: an anode, 3: a hole-injecting layer, 4: a hole-transporting layer, 5: a light-emitting layer, 6: an electron-transporting layer, 7: a cathode.

DESCRIPTION OF EMBODIMENTS

A material for organic electroluminescent devices of the present invention is an ortho-carborane compound represented by the general formula (1). The ortho-carborane compound exhibits such excellent effects as described above probably because the compound has a structure of being substituted with an aromatic hydrocarbon group or an aromatic heterocycle having bonded thereto a silyl group. Symbols common to the general formulae (1) and (2) are interpreted as having the same meanings.

In the general formula (1), $L_1$ and $L_2$ each independently represent a substituted or unsubstituted aromatic hydrocarbon group having 6 to 30 carbon atoms, a substituted or unsubstituted aromatic heterocyclic group having 3 to 30 carbon atoms, or a linked aromatic group formed by linking 2 to 6 aromatic rings of aromatic groups selected from the aromatic hydrocarbon group and the aromatic heterocyclic group, and when the aromatic rings are linked, the linked aromatic group may be linear or branched, and the aromatic rings to be linked may be identical to or different from each other. $L_1$ and $L_2$ each preferably represent a substituted or unsubstituted aromatic hydrocarbon group having 6 to 18 carbon atoms, a substituted or unsubstituted aromatic heterocyclic group having 3 to 17 carbon atoms, or a linked aromatic group formed by linking 2 to 4 aromatic rings of the aromatic hydrocarbon group, the substituted or unsubstituted aromatic heterocyclic group having 3 to 17 carbon atoms, or the aromatic hydrocarbon group and the aromatic heterocyclic group. It should be noted that $L_1$ represents a p+1-valent group and $L_2$ represents a q+1-valent group.

Specific examples of the unsubstituted aromatic hydrocarbon group include groups each produced by removing a hydrogen atom from an aromatic hydrocarbon compound, such as benzene, naphthalene, fluorene, anthracene, phenanthrene, fluoranthene, pyrene, chrysene, or triphenylene, or an aromatic hydrocarbon compound in which a plurality of these compounds are linked to each other. Of those, a group produced by removing a hydrogen atom from benzene, naphthalene, anthracene, phenanthrene, or triphenylene is preferred.

Specific examples of the unsubstituted aromatic heterocyclic group include linking groups each produced by removing a hydrogen atom from an aromatic heterocyclic compound, such as pyridine, pyrimidine, triazine, quinoline, isoquinoline, quinoxaline, naphthyridine, carbazole, dibenzofuran, dibenzothiophene, acridine, azepine, tribenzazepine, phenazine, phenoxazine, phenothiazine, dibenzophosphole, or dibenzoborole, or an aromatic heterocyclic compound in which a plurality of these compounds are linked to each other. Of those, a group produced by removing a hydrogen atom from pyridine, pyrimidine, triazine, carbazole, dibenzofuran, or dibenzothiophene is preferred.

A group produced by removing a hydrogen atom from an aromatic compound having a structure in which a plurality of aromatic rings of aromatic hydrocarbon compounds or aromatic heterocyclic compounds are linked to each other is referred to as "linked aromatic group." The linked aromatic group is a group formed by linking 2 to 6 aromatic rings, the aromatic rings to be linked may be identical to or different from each other, and both an aromatic hydrocarbon group and an aromatic heterocyclic group may be included. The number of the aromatic rings to be linked is preferably from 2 to 4, more preferably 2 or 3.

Specific examples of the linked aromatic group include groups each produced by removing a hydrogen atom from biphenyl, terphenyl, phenylnaphthalene, diphenylnaphthalene, phenylanthracene, diphenylanthracene, diphenylfluorene, bipyridine, bipyrimidine, bitriazine, biscarbazole, bisdibenzofuran, bisdibenzothiophene, phenylpyridine, phenylpyrimidine, phenyltriazine, phenylcarbazole, phenyldibenzofuran, phenyldibenzothiophene, diphenylpyridine, diphenyltriazine, bis(carbazolyl)benzene, bis(dibenzofuranyl)benzene, bis(dibenzothiophenyl)benzene, or the like.

The aromatic hydrocarbon group, the aromatic heterocyclic group, or the linked aromatic group may have a substituent, and when any such group has a substituent, a preferred substituent is an alkyl group having 1 to 12 carbon atoms, an alkoxy group having 1 to 12 carbon atoms, a cyano group, or an acetyl group. A more preferred substituent is an alkyl group having 1 to 4 carbon atoms, an alkoxy group having 1 or 2 carbon atoms, or an acetyl group.

Here, when the linked aromatic group is a divalent group, the group is represented by, for example, any one of the following formulae, and its aromatic rings may be linked in a linear manner or a branched manner.

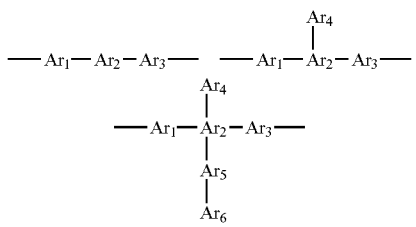

In the formulae, $Ar_1$ to $Ar_6$ each represent an unsubstituted aromatic hydrocarbon ring or aromatic heterocycle.

In the general formula (1), p represents an integer of from 1 to 5, preferably from 1 to 2. q represents an integer of from 0 to 5, preferably from 0 to 2. r represents an integer of from 1 to 4, preferably from 1 to 2. p+q is preferably from 1 to 5, more preferably 1 or 2.

In the general formula (1), $R_1$ to $R_6$ each independently represent an aliphatic hydrocarbon group having 1 to 12 carbon atoms, an aromatic hydrocarbon group having 6 to 18 carbon atoms, or an aromatic heterocyclic group having 3 to 17 carbon atoms. $R_1$ to $R_6$ each preferably represent an aliphatic hydrocarbon group having 1 to 10 carbon atoms, or an aromatic hydrocarbon group having 6 to 12 carbon atoms. It should be noted that the aliphatic hydrocarbon group may be saturated or unsaturated, and may be linear, branched, or cyclic, but is more preferably an alkyl group.

Specific examples of $R_1$ to $R_6$ include: alkyl groups, such as a methyl group, an ethyl group, a propyl group, an isopropyl group, a butyl group, a pentyl group, a hexyl group, and an octyl group; cycloalkyl groups, such as a cyclopentyl group and a cyclohexyl group; and aromatic hydrocarbon groups or aromatic heterocyclic groups, such as a phenyl group, a pyridyl group, a pyrimidyl group, a triazyl group, a naphthyl group, a quinolyl group, an isoquinolyl group, a quinazolyl group, a phthalazyl group, a fluorenyl group, a carbazolyl group, a dibenzofuranyl group, and a dibenzothiophenyl group. Of those, a phenyl group, a pyridyl group, a pyrimidyl group, a triazyl group, a naphthyl group, a quinolyl group, an isoquinolyl group, a fluorenyl group, or a carbazolyl group is preferred.

These groups may each further have a substituent, and the substituent is preferably an alkyl group having 1 to 4 carbon atoms, an alkoxy group having 1 or 2 carbon atoms, an acetyl group, a cyano group, an aromatic hydrocarbon group having 6 to 12 carbon atoms, or an aromatic heterocyclic group having 3 to 12 carbon atoms. Specific examples thereof include a methyl group, an ethyl group, an isopropyl group, a butyl group, a methoxy group, an ethoxy group, an acetyl group, a phenyl group, a pyridyl group, a pyrimidyl group, a triazyl group, a naphthyl group, a quinolyl group, an isoquinolyl group, a fluorenyl group, a carbazolyl group, a dibenzofuranyl group, a dibenzothiophenyl group, and a cyano group. In the case where $R_1$ to $R_6$ each represent an aromatic hydrocarbon group or an aromatic heterocyclic group, and a substituent thereof is an aromatic hydrocarbon group or an aromatic heterocyclic group, such group is referred to as "linked aromatic group" in the description of $L_1$ or $L_2$. Even in such case, however, the group is treated as a substituted aromatic group in description except the description of $L_1$ or $L_2$.

In the general formula (1), $R_7$ and $R_8$ each independently represent hydrogen, an aliphatic hydrocarbon group having 1 to 12 carbon atoms, an aromatic hydrocarbon group having 6 to 18 carbon atoms, or an aromatic heterocyclic group having 3 to 17 carbon atoms. $R_7$ and $R_8$ each preferably represent hydrogen, an aliphatic hydrocarbon group having 1 to 8 carbon atoms, an aromatic hydrocarbon group having 6 to 12 carbon atoms, or an aromatic heterocyclic group having 3 to 12 carbon atoms. The groups are the same as those described for $R_1$ to $R_6$ except that hydrogen is included.

In the general formula (1), a ring A represents a divalent ortho-carborane group $C_2B_{10}H_{10}$ represented by the formula (1a). The two bonding hands of the formula (1a) may each be produced from C or may each be produced from B, but a bonding hand to be bonded to $L_1$ or $L_2$ is preferably produced from C. It should be noted that part or all of the hydrogen atoms of the ortho-carborane compound may each be substituted with deuterium.

For example, as an ortho-carborane parent skeleton, (A-1) may be synthesized in accordance with the following reaction formula with reference to a synthesis example described in Macromolecules, 2010, 43, p 6463-6468.

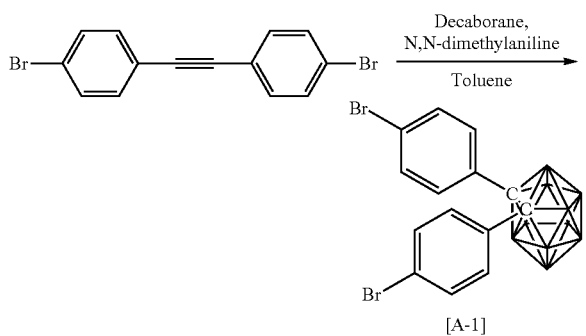

(A-2) may be synthesized in accordance with the following reaction formula with reference to synthesis examples described in European Journal of Inorganic Chemistry, 2010, p 2012-2024 and Inorganic Chemistry, 1995, 34, p 2095-2100.

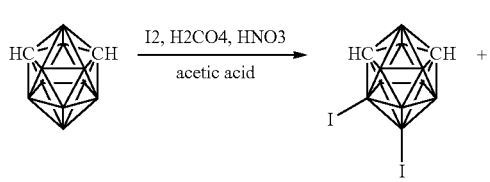

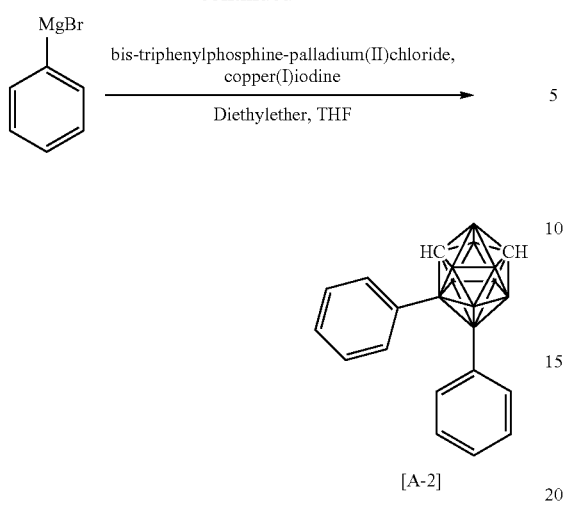
[A-2]
Specific examples of the ortho-carborane compound represented by the general formula (1) or (2) are shown below. However, the material for organic electroluminescent devices of the present invention is not limited thereto.
1
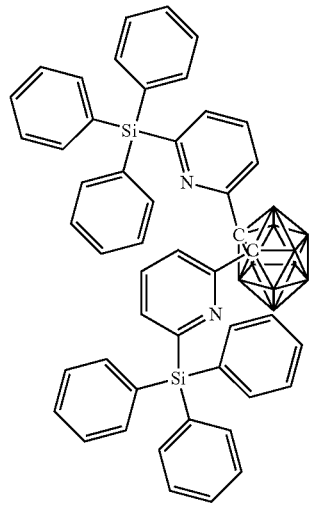
2
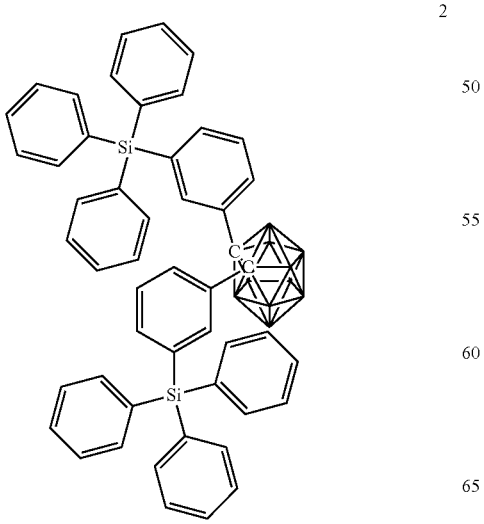
3
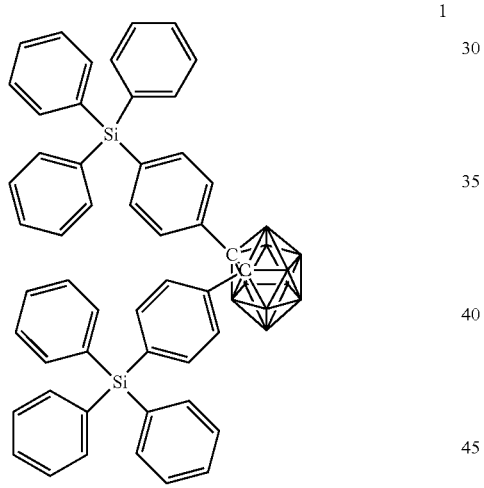
4
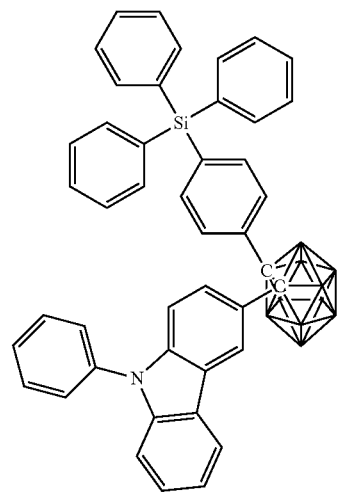
5
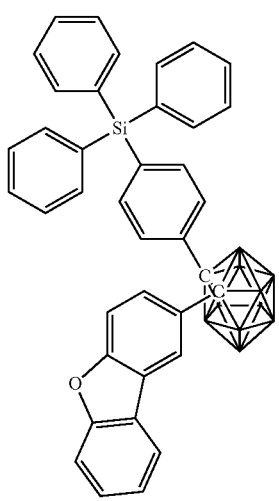

6
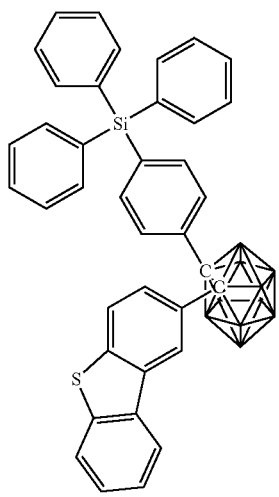
7
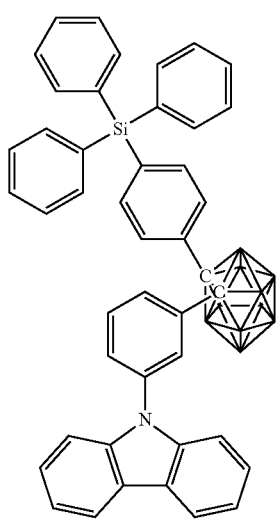
8
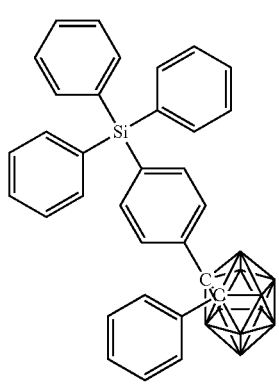
9
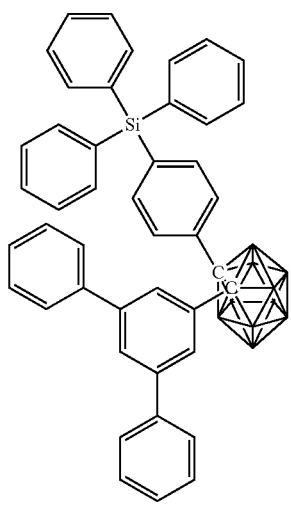
10
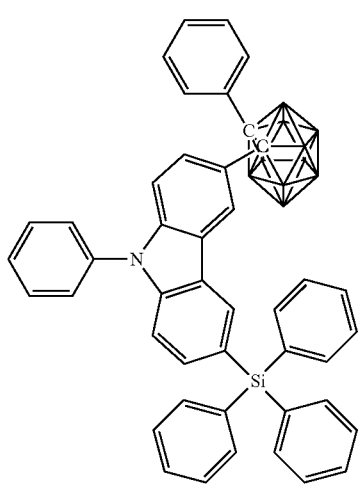
11
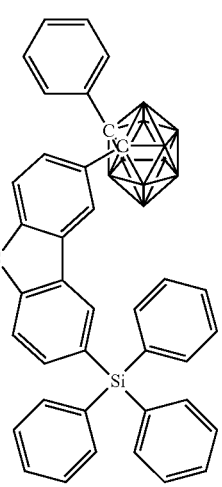

12
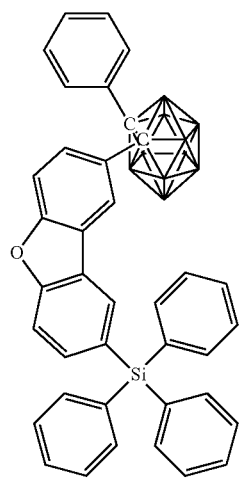
13
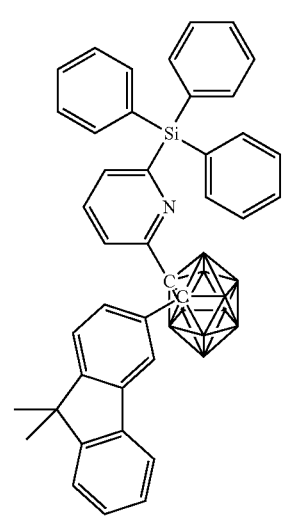
14
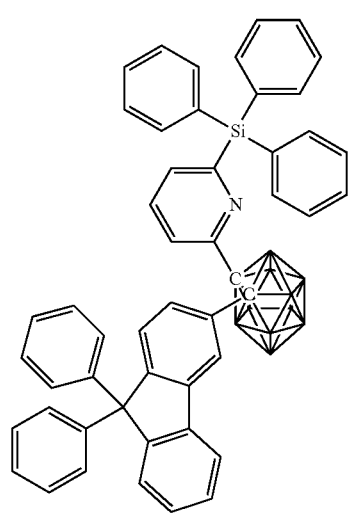
15
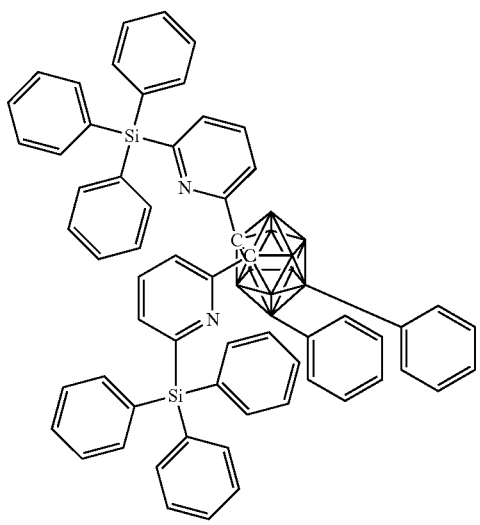
16
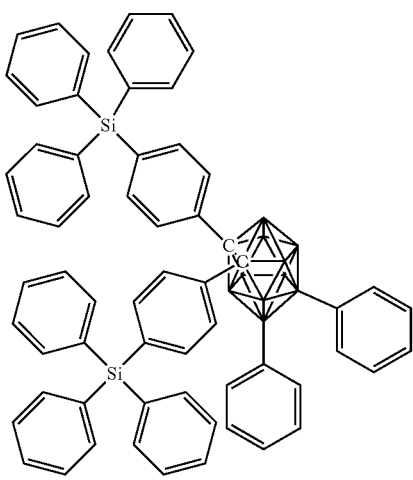
17
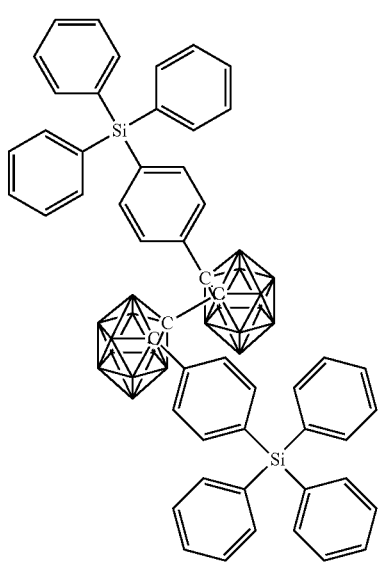

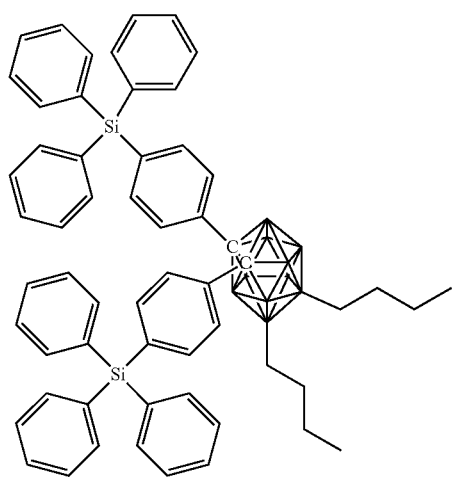
18
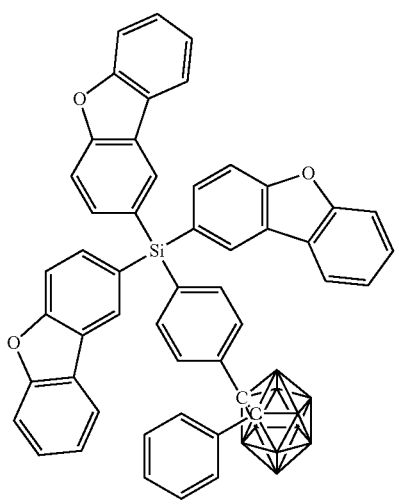
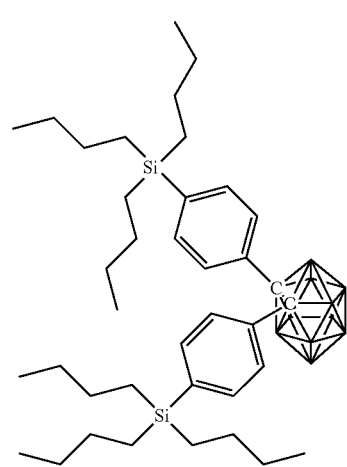
19
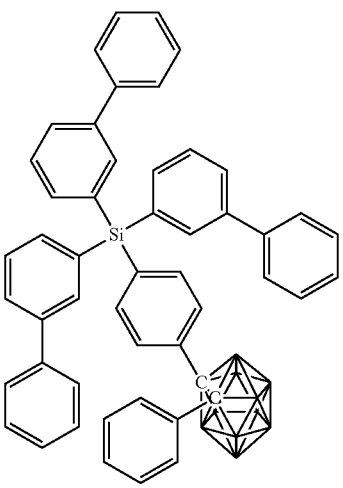
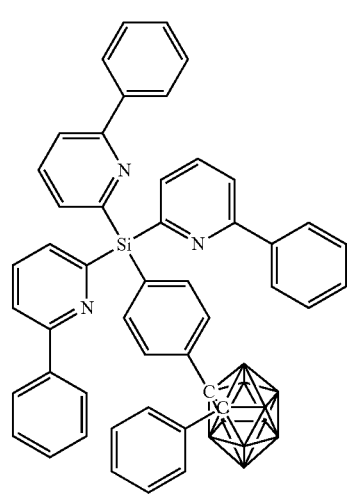
20
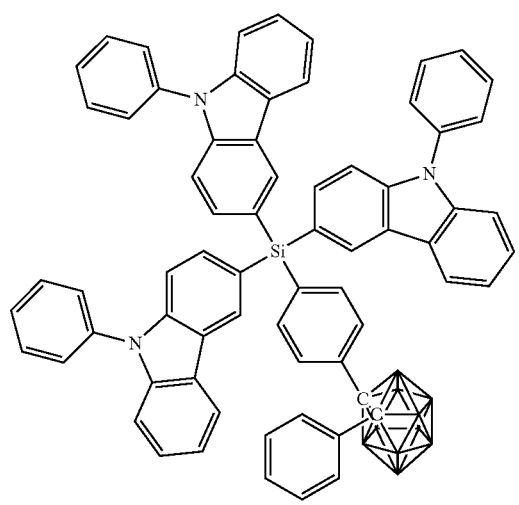

24
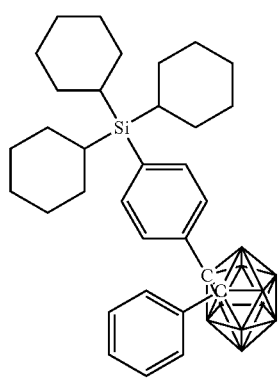
25
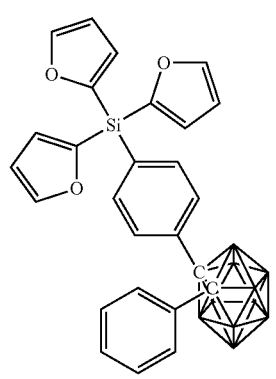
26
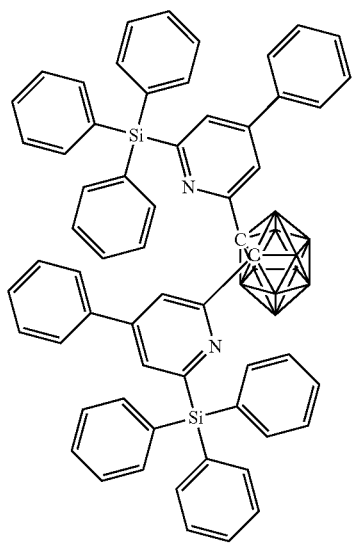
27
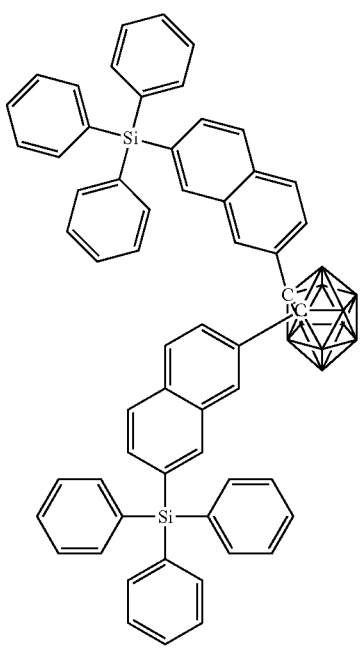
28
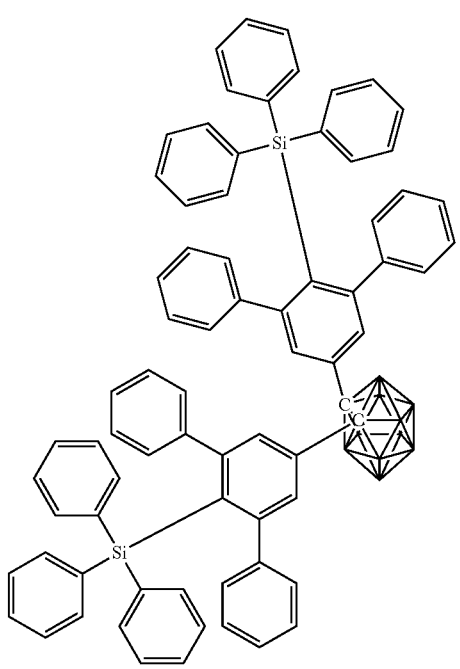

29
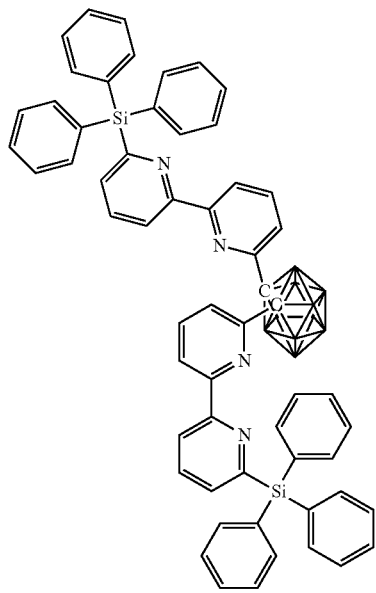
30
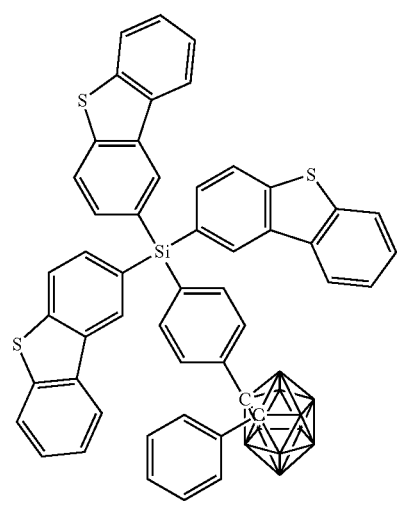
31
32
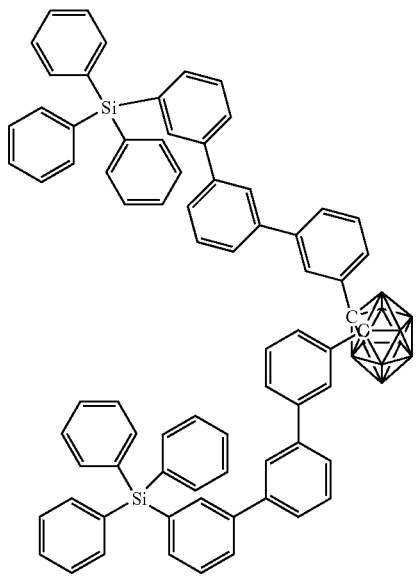
33
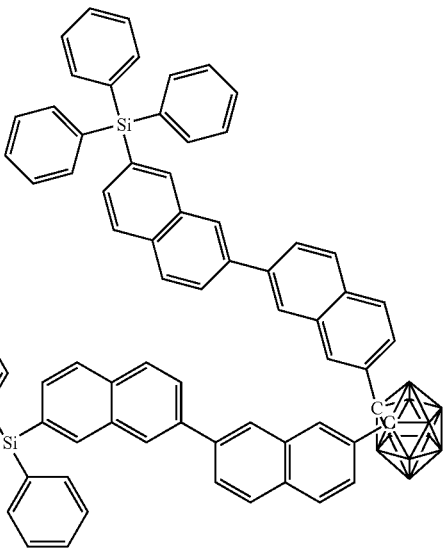

-continued

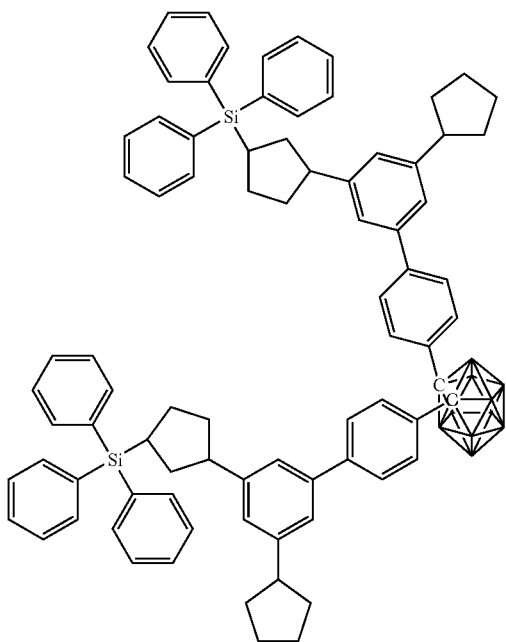

34

When the material for organic electroluminescent devices of the present invention is contained in at least one of a plurality of organic layers of an organic EL device having a structure in which an anode, the plurality of organic layers, and a cathode are laminated on a substrate, an excellent organic electroluminescent device is provided. A light-emitting layer, an electron-transporting layer, a hole-blocking layer, or an exciton-blocking layer is suitable as the organic layer in which the material for organic electroluminescent devices of the present invention is contained. Here, when the compound of the present invention is used in the light-emitting layer, the compound can be used as a host material for the light-emitting layer containing a fluorescent light-emitting, delayed fluorescent light-emitting, or phosphorescent light-emitting dopant. In addition, the compound of the present invention can be used as an organic light-emitting material that radiates fluorescence and delayed fluorescence. When the compound of the present invention is used as an organic light-emitting material that radiates fluorescence and delayed fluorescence, any other organic compound having a value for at least one of excited singlet energy or excited triplet energy higher than that of the compound is preferably used as the host material. The compound of the present invention is particularly preferably incorporated as a host material for the light-emitting layer containing the phosphorescent light-emitting dopant.

Next, an organic EL device using the material for organic electroluminescent devices of the present invention is described.

The organic EL device of the present invention includes organic layers including at least one light-emitting layer between an anode and a cathode laminated on a substrate. In addition, at least one of the organic layers contains the material for organic electroluminescent devices of the present invention. The material for organic electroluminescent devices of the present invention is advantageously contained in the light-emitting layer, an electron-transporting layer, a hole-blocking layer, or an exciton-blocking layer. In particular, the material for organic electroluminescent devices of the present invention is preferably contained in an electron-transporting layer, a hole-blocking layer, or an exciton-blocking layer.

Next, the structure of the organic EL device of the present invention is described with reference to the drawings. However, the structure of the organic EL device of the present invention is by no means limited to one illustrated in the drawings.

FIG. 1 is a sectional view for illustrating an example of the structure of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may include an exciton-blocking layer adjacent to the light-emitting layer, or may include a hole-blocking layer between the light-emitting layer and the electron-transporting layer. The exciton-blocking layer may be inserted on any of the anode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure as compared to FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. In addition, a material such as IDIXO ($In_2O_3$—ZnO) which can produce an amorphous, transparent conductive film, may be used. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance, such as an organic conductive compound, is used, a wet film-forming method, such as a printing method or a coating method, may be used. When luminescence is taken out from the anode, the transmittance of the anode is desirably controlled to more than 10%. In addition, the sheet resistance of the anode is preferably several hundred ohms per square ($\Omega/\square$) or less. Further, the thickness of the film is, depending on its material, selected from the range of generally from 10 nm to 1,000 nm, preferably from 10 nm to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal, which is a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum, is suitable from the viewpoints of an electron-injecting property and durability against oxidation or the like. The cathode can be produced by forming any of those electrode substances into a thin film by using a method such as vapor deposition or sputtering. In addition, the sheet resistance of the cathode is preferably several hundred $\Omega/\square$ or less, and the thickness of the film is selected from the range of generally from 10 nm to 5 μm, preferably from 50 nm to 200 nm. It should be noted that, in order for luminescence produced to pass through, any one of the anode and cathode of the organic EL device is preferably transparent or semi-transparent, because the light emission luminance improves.

In addition, after the above-mentioned metal has been formed into a film having a thickness of from 1 nm to 20 nm as a cathode, the conductive transparent material mentioned in the description of the anode is formed into a film on the cathode, thereby being able to produce a transparent or semi-transparent cathode. Through the application of this, a device in which both the anode and cathode have transparency can be produced.

—Light-Emitting Layer—

The light-emitting layer is a layer that emits light after the production of an exciton by the recombination of a hole injected from the anode and an electron injected from the cathode, and the light-emitting layer contains an organic light-emitting material and a host material When the light-emitting layer is a fluorescent light-emitting layer, at least one kind of fluorescent light-emitting material may be used alone as the fluorescent light-emitting material. However, it is preferred that the fluorescent light-emitting material be used as a fluorescent light-emitting dopant and the host material be contained.

The ortho-carborane compound represented by the general formula (1) can be used as the fluorescent light-emitting material in the light-emitting layer. However, the fluorescent light-emitting material is known through, for example, many patent literatures, and hence can be selected therefrom. Examples thereof include a benzoxazole derivative, a benzothiazole derivative, a benzimidazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, a pyrrolidine derivative, a cyclopentadiene derivative, a bis-styrylanthracene derivative, a quinacridone derivative, a pyrrolopyridine derivative, a thiadiazolopyridine derivative, a styrylamine derivative, a diketopyrrolopyrrole derivative, an aromatic dimethylidene compound, various metal complexes typified by a metal complex of an 8-quinolinol derivative, and a metal complex, rare earth complex, or transition metal complex of a pyrromethene derivative, polymer compounds such as polythiophene, polyphenylene, and polyphenylene vinylene, and an organic silane derivative. Of those, for example, the following compound is preferred: a fused aromatic compound, a styryl compound, a diketopyrrolopyrrole compound, an oxazine compound, or a pyrromethene metal complex, transition metal complex, or lanthanoid complex. For example, the following compound is more preferred: naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthaphenanthridine, phenanthroxazole, quinolino[6,5-f]quinoline, or benzothiophanthrene. Those compounds may each have an alkyl group, aryl group, aromatic heterocyclic group, or diarylamino group as a substituent.

The ortho-carborane compound represented by the general formula (1) can be used as a fluorescent host material in the light-emitting layer. However, the fluorescent host material is known through, for example, many patent literatures, and hence can be selected therefrom. For example, the following material can be used: a compound having a fused aryl ring, such as naphthalene, anthracene, phenanthrene, pyrene, chrysene, naphthacene, triphenylene, perylene, fluoranthene, fluorene, or indene, or a derivative thereof; an aromatic amine derivative, such as N,N'-dinaphthyl-N,N'-diphenyl-4,4'-diphenyl-1,1'-diamine; a metal chelated oxinoid compound typified by tris(8-quinolinato)aluminum (III); a bisstyryl derivative, such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative, such as a polyphenylene vinylene derivative, a poly-p-phenylene derivative, a polyfluorene derivative, a polyvinyl carbazole derivative, or a polythiophene derivative. However, the fluorescent host material is not particularly limited thereto.

When the fluorescent light-emitting material is used as a fluorescent light-emitting dopant and the host material is contained, the content of the fluorescent light-emitting dopant in the light-emitting layer desirably falls within the range of from 0.01 wt % to 20 wt %, preferably from 0.1 wt % to 10 wt %.

An organic EL device typically injects charges from both of its electrodes, i.e., its anode and cathode into a light-emitting substance to produce a light-emitting substance in an excited state, and causes the substance to emit light. In the case of a charge injection-type organic EL device, it is said that 25% of the produced excitons are excited to a singlet excited state and the remaining 75% of the excitons are excited to a triplet excited state. As described in Advanced Materials 2009, 21, 4802-4806, it has been known that after a specific fluorescent light-emitting substance has undergone an energy transition to a triplet excited state as a result of intersystem crossing or the like, the substance is subjected to inverse intersystem crossing to a singlet excited state by triplet-triplet annihilation or the absorption of thermal energy to radiate fluorescence, thereby expressing thermally activated delayed fluorescence. The organic EL device of the present invention can also express delayed fluorescence. In this case, the light emission can include both fluorescent light emission and delayed fluorescent light emission. It should be noted that light emission from the host material may be present in part of the light emission.

When the light-emitting layer is a phosphorescent light-emitting layer, the light-emitting layer contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold.

Preferred examples of the phosphorescent light-emitting dopant include complexes such as Ir(ppy)$_3$, complexes such as Ir(bt)$_2$.acac$_3$, and complexes such as PtOEt$_3$, the complexes each having a noble metal element, such as Ir, as a central metal. Specific examples of those complexes are shown below, but the complexes are not limited to the compounds described below.

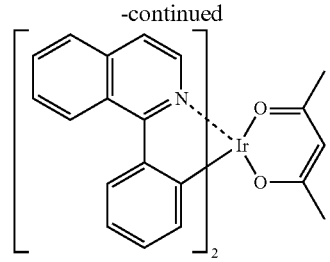

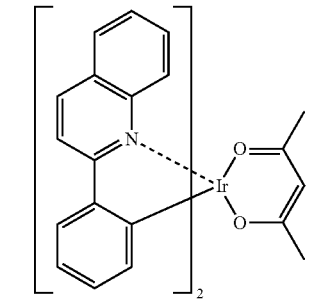

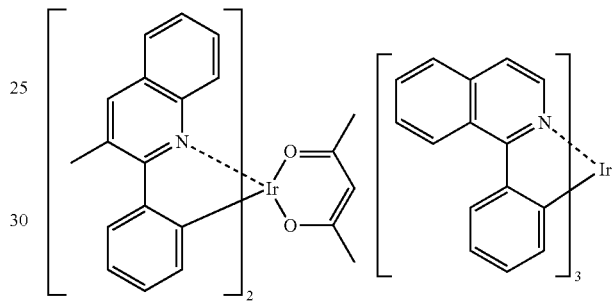

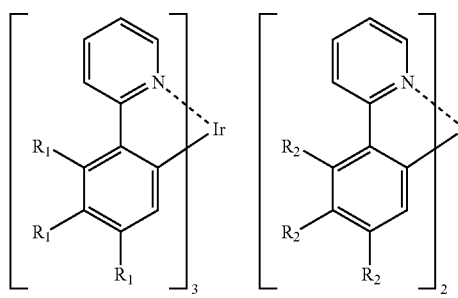

R1: H, CH$_3$, CF$_3$, F    R2: H, F

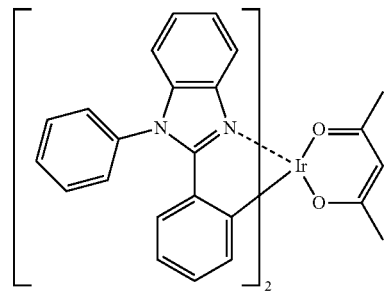

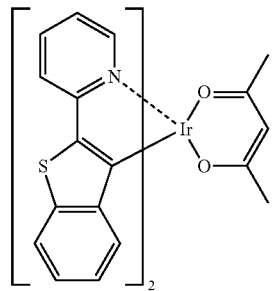

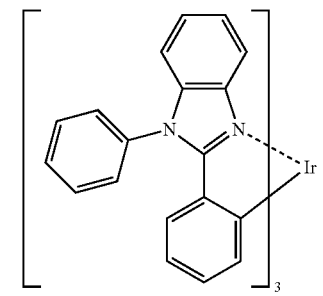

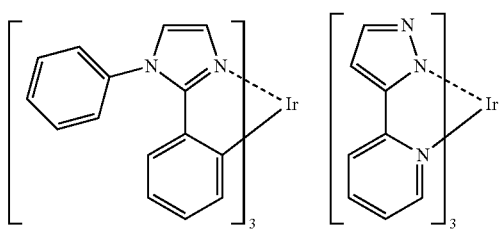
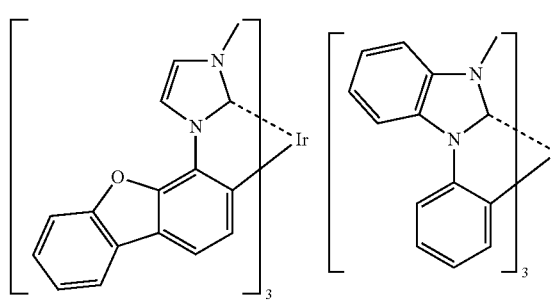
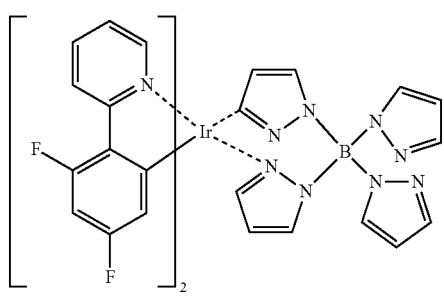
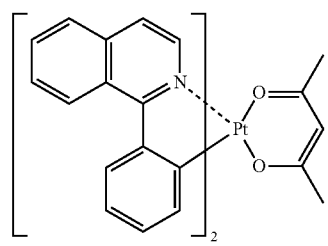
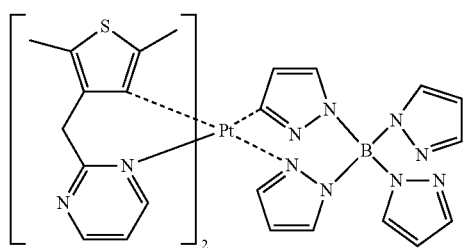

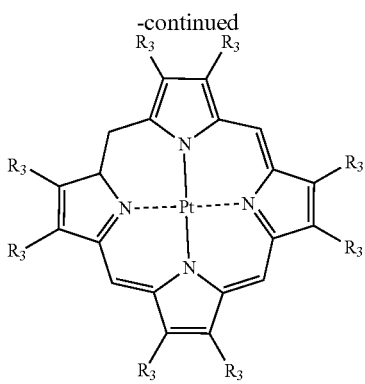

R3: CH$_3$, CH$_2$CH$_3$

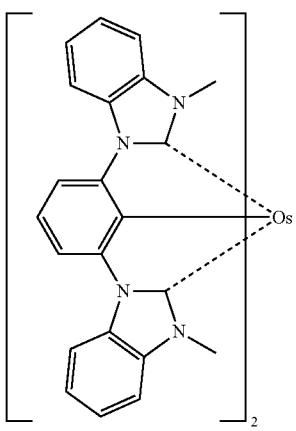

It is preferred that the content of the phosphorescent light-emitting dopant in the light-emitting layer fall within the range of from 2 wt % to 40 wt %, preferably from 5 wt % to 30 wt %.

When the light-emitting layer is a phosphorescent light-emitting layer, it is preferred to use, as a host material in the light-emitting layer, the ortho-carborane compound represented by the general formula (1) according to the present invention. However, when the ortho-carborane compound is used in any other organic layer except the light-emitting layer, the material to be used in the light-emitting layer may be another host material except the ortho-carborane compound. In addition, the ortho-carborane compound and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Any such other host material is known through, for example, many patent literatures, and hence can be selected therefrom. Specific examples of the host material include, but are not particularly limited to, an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride, such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds, such as a polysilane-based compound, a poly (N-vinylcarbazole) derivative, an aniline-based copolymer, a thiophene oligomer, a polythiophene derivative, a polyphenylene derivative, a polyphenylenevinylene derivative, and a polyfluorene derivative.

The light-emitting layer, which may be any one of a fluorescent light-emitting layer, a delayed fluorescent light-emitting layer, and a phosphorescent light-emitting layer, is preferably the phosphorescent light-emitting layer.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use the ortho-carborane compound represented by the general formula (1) according to the present invention for the hole-blocking layer. However, when the ortho-carborane compound is used in any other organic layer, a known material for a hole-blocking layer may be used. In addition, a material for the electron-transporting layer to be described later can be used as a material for the hole-blocking layer as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

A material for the hole-transporting layer to be described later can be used as a material for the electron-blocking layer as required. The thickness of the electron-blocking layer is preferably from 3 nm to 100 nm, more preferably from 5 nm to 30 nm.

—Exciton-Blocking Layer—

The exciton-blocking layer refers to a layer for blocking excitons produced by the recombination of a hole and an electron in the light-emitting layer from diffusing into charge-transporting layers. The insertion of this layer enables efficient confinement of the excitons in the light-emitting layer, thereby being able to improve the luminous efficacy of the device. The exciton-blocking layer can be inserted on any of the anode side and the cathode side of the adjacent light-emitting layer, and can also be inserted simultaneously on both sides.

Although the ortho-carborane compound represented by the general formula (1) can be used as a material for the exciton-blocking layer, as other materials therefor, there are given, for example, 1,3-dicarbazolylbenzene (mCP) and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers can be formed.

The hole-transporting material has a hole-injecting property or a hole-transporting property or has an electron-blocking property, and any of an organic material and an inorganic material can be used as the hole-transporting material. Although the ortho-carborane compound represented by the general formula (1) can be used as a hole-transporting material that can be used, it is preferred to use any compound selected from conventionally known compounds. Examples of the known hole-transporting material that can be used include a triazole derivative, an oxadiazole derivative an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers can be formed.

An electron-transporting material (which also serves as a hole-blocking material in some cases) only needs to have a function of transferring electrons injected from the cathode into the light-emitting layer. Although it is preferred to use the ortho-carborane derivative represented by the general formula (1) according to the present invention for the electron-transporting layer, any compound selected from conventionally known compounds can be used. Examples thereof include a nitro-substituted fluorene derivative, a diphenylquinone derivative, a thiopyran dioxide derivative, a carbodiimide, a fluorenylidenemethane derivative, anthraquinodimethane, an anthrone derivative, and an oxadiazole derivative. Further, a thiadiazole derivative prepared by substituting an oxygen atom on an oxadiazole ring with a sulfur atom in the oxadiazole derivative or a quinoxaline derivative that has a quinoxaline ring known as an electron withdrawing group can be used as the electron-transporting material. Further, a polymer material in which any such material is introduced in a polymer chain or is used as a polymer main chain can be used.

EXAMPLES

Now, the present invention is described in more detail by way of Examples. It should be appreciated that the present invention is not limited to Examples below and can be carried out in various forms as long as the various forms do not deviate from the gist of the present invention.

The route described below was used to synthesize an ortho-carborane compound to be used as a material for organic electroluminescent devices. It should be noted that the number of each compound corresponds to the number given to the chemical formula.

Example 1

A compound 1 is synthesized in accordance with the following reaction formulae.

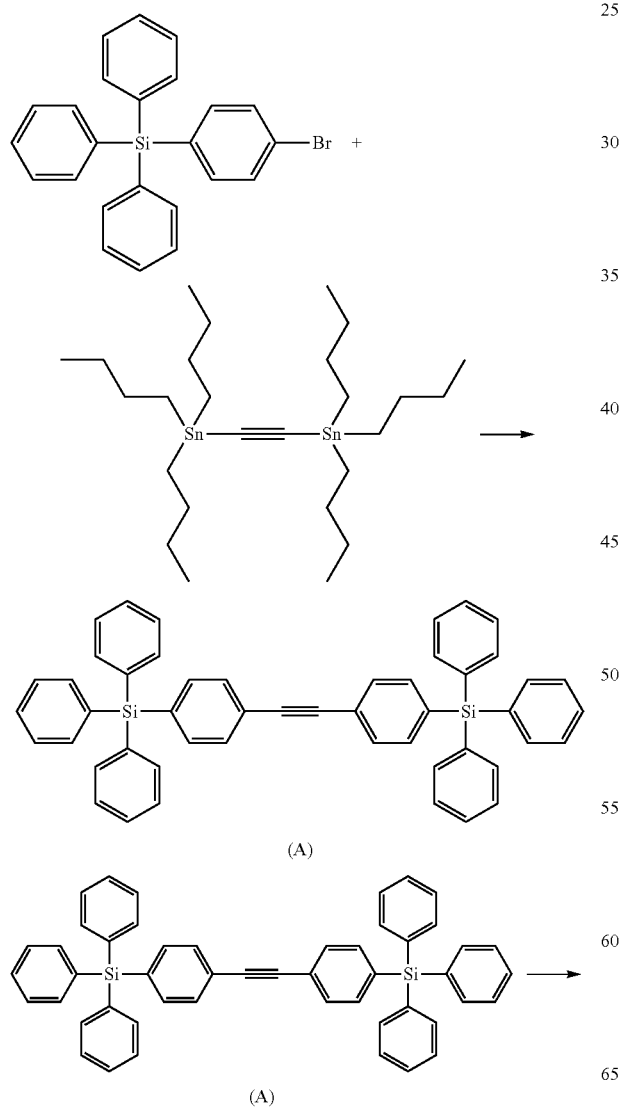

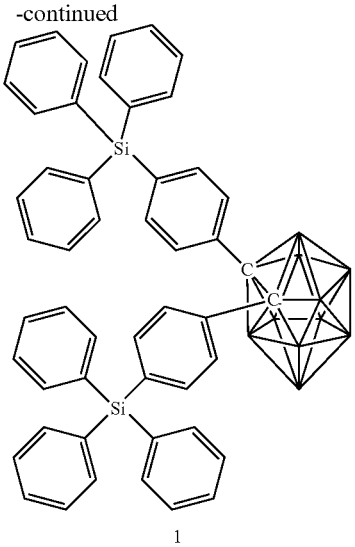

1

Under a nitrogen atmosphere, 1.72 g (0.00149 mol) of tetrakis(triphenylphosphine)palladium(0), 34.3 g (0.0825 mol) of 4-bromotetraphenylsilane, 25.0 g (0.0412 mol) of bis(tributylstannyl) acetylene, and 300 mL of 1,4-dioxane were added, and the mixture was stirred at 120° C. overnight. The reaction solution was cooled to room temperature, and then the precipitated crystal was taken by filtration and the resultant solid was purified by silica gel column chromatography to provide 13.0 g (18.7 mmol, 45.3% yield) of an intermediate A as a white solid.

Figure 2:
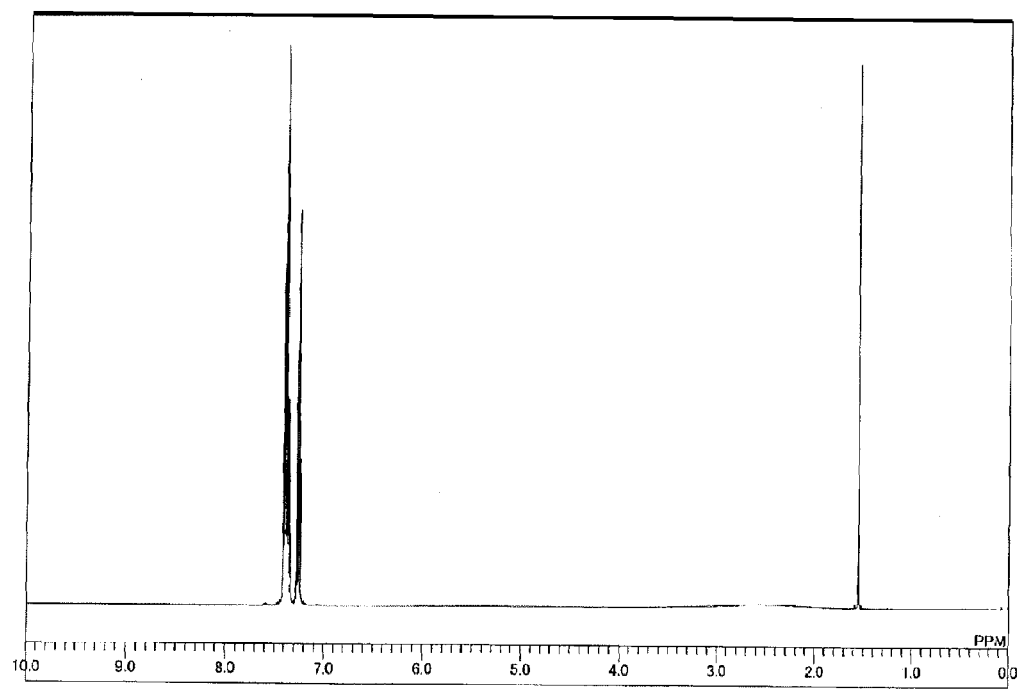
FIG. 2 is an NMR chart of an ortho-carborane compound 1.

Under a nitrogen atmosphere, 2.23 g (0.0186 mol) of decaborane and 229 mL of toluene were added, and decaborane was completely dissolved in toluene. 2.34 mL of N,N-dimethylaniline was dropped to the solution and the mixture was stirred at room temperature for 30 min. After that, 13.0 g (18.7 mmol) of the intermediate A was added to the resultant and the mixture was stirred at 120° C. overnight. The reaction solution was cooled to room temperature, and then the precipitated crystal was taken by filtration and the resultant solid was purified by crystallization to provide 8.01 g (9.83 mmol, 52.8% yield) of the compound 1 as a white solid. The FD-MS of the compound showed an [M+H]$^+$ ion peak at an m/z of 814. The results of its $^1$H-NMR measurement (measurement solvent: CDCl$_3$) are shown in FIG. 2.

Example 2

A compound 3 is synthesized in accordance with the following reaction formulae.

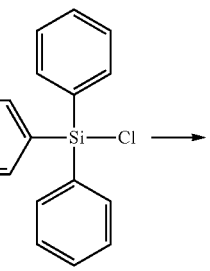

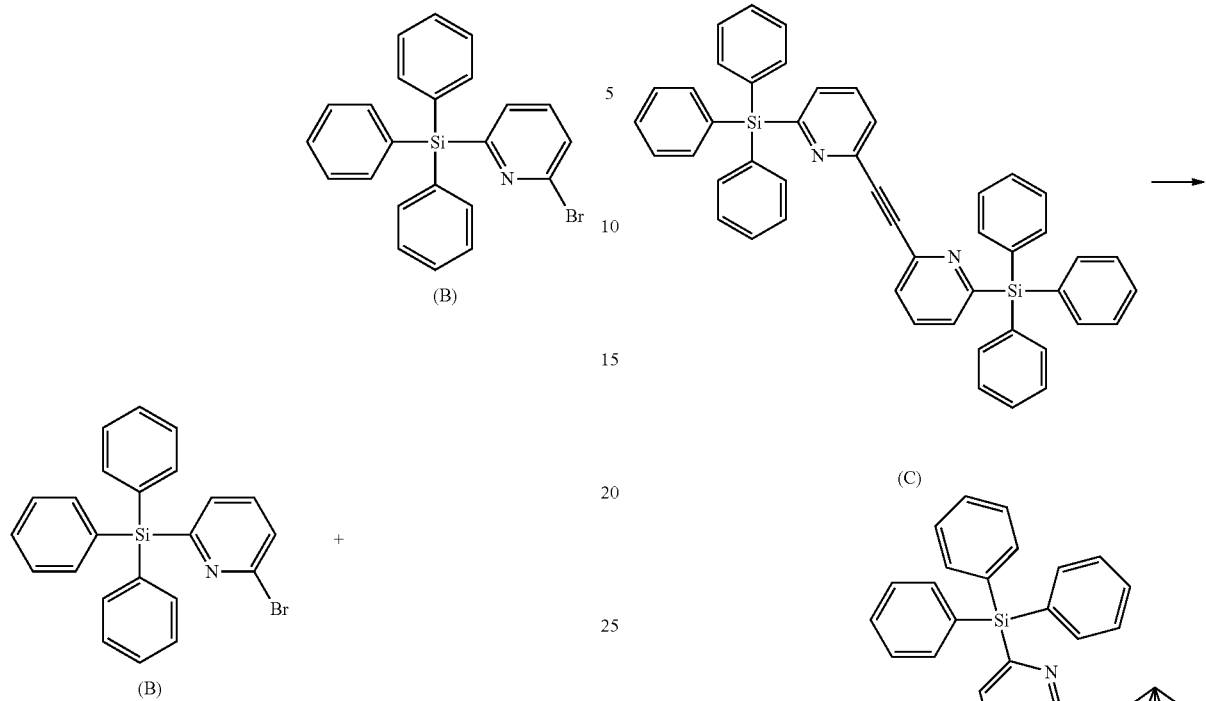

(B)

(B)

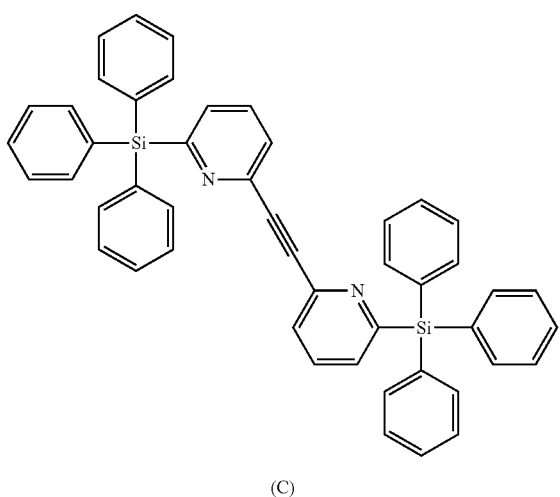

(C)

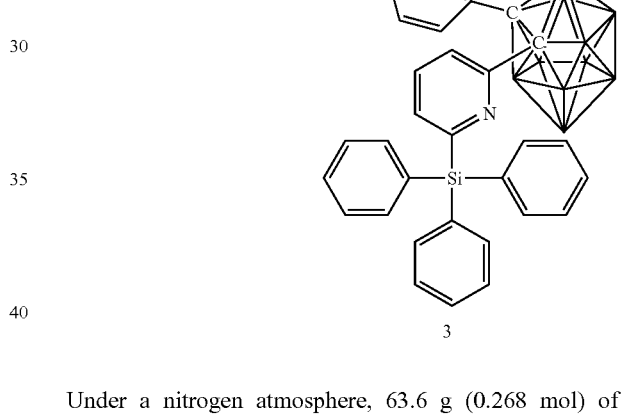

(C)

3

Under a nitrogen atmosphere, 63.6 g (0.268 mol) of 2,6-dibromopyridine and 1,080 mL of tetrahydrofuran (THF) were added, and the mixture was cooled to −50° C. After that, a 2.69 M solution of n-butyllithium in hexane was dropped to the mixture, and the whole was stirred at −50° C. for 2 hr. 78.4 g (0.266 mol) of triphenylchlorosilane dissolved in 240 ml of THF and 160 ml of diethyl ether was dropped to the resultant black solution. After that, the mixture was stirred overnight while its temperature was gradually increased to room temperature. Ethyl acetate (1,000 mL) and 1 N hydrochloric acid (1,000 mL) were added to the resultant reaction liquid while the liquid was stirred, followed by the washing of an organic layer with distilled water (3×500 mL) The organic layer was dried with anhydrous magnesium sulfate, and then magnesium sulfate was separated by filtration and the solvent was distilled off under reduced pressure. The resultant residue was purified by silica gel column chromatography to provide 18.5 g (44.4 mmol, 17% yield) of an intermediate B as a white solid.

Under a nitrogen atmosphere, 665 mg (0.575 mmol) of tetrakis(triphenylphosphine) palladium (0), 28 g (0.0672 mol) of the intermediate B, 19.4 g (0.0320 mol) of bis(tributylstannyl) acetylene, and 245 mL of 1,4-dioxane were added, and the mixture was stirred at 120° C. overnight. The reaction solution was cooled to room temperature, and then the precipitated crystal was taken by filtration and the solvent was distilled off under reduced pressure. The resultant residue was purified by crystallization and silica gel column chromatography to provide 12.4 g (17.8 mmol, 55.7% yield) of an intermediate C as a white solid.

Figure 3:
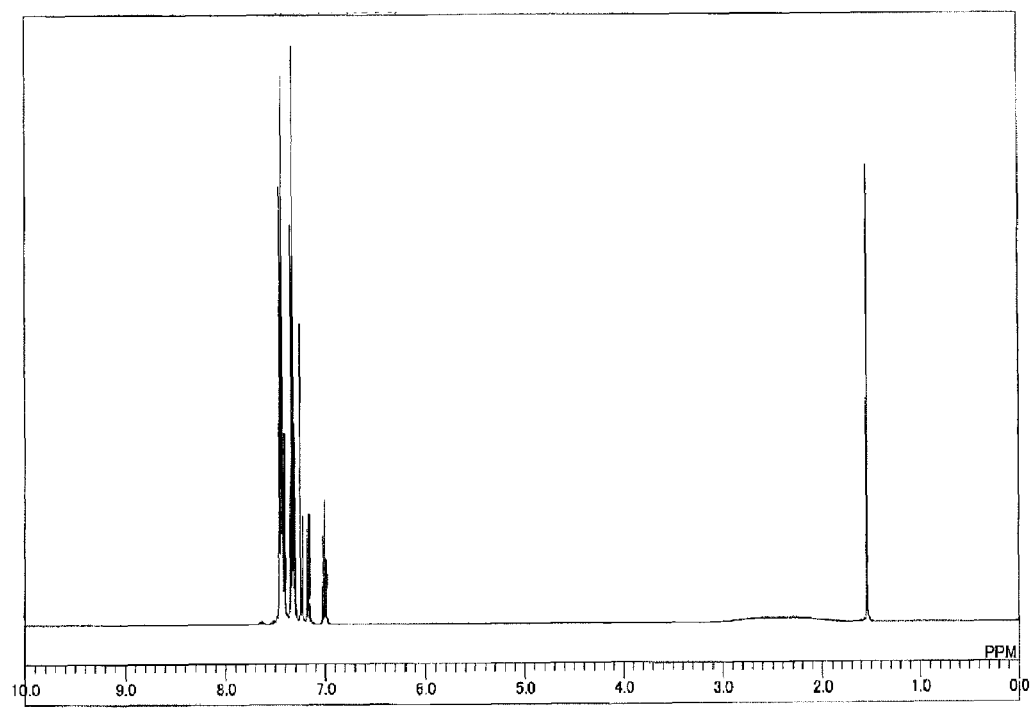
FIG. 3 is an NMR chart of an ortho-carborane compound 3.

Under a nitrogen atmosphere, 2.0 g (0.0164 mol) of decaborane and 200 mL of toluene were added, and decaborane was completely dissolved in toluene. 2.12 mL of N,N-dimethylaniline was dropped to the solution and the mixture was stirred at room temperature for 30 min. After that, 12.4 g (17.8 mmol) of the intermediate C was added to the resultant and the mixture was stirred at 120° C. overnight. The reaction solution was cooled to room temperature, and then the precipitated crystal was taken by filtration, and the resultant solid was purified by crystallization and silica gel column chromatography to provide 2.6 g (3.19 mmol, 19.5% yield) of the compound 3 as a white solid. The APCI-TOFMS of the compound showed an [M+H]$^+$ ion peak at an m/z of 816. The results of its $^1$H-NMR measurement (measurement solvent: CDCl$_3$) are shown in FIG. 3.

Compounds 10, 16, 17, 22, and 23 were synthesized in conformity with the synthesis examples. In addition, the following compounds H-1 to H-4 were synthesized as compounds for comparison.

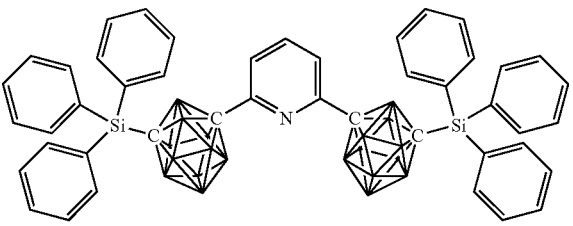

Example 3

Each thin film was laminated by a vacuum deposition method at a degree of vacuum of 2.0×10$^{-5}$ Pa on a glass substrate on which an anode formed of ITO having a thickness of 70 nm had been formed. First, CuPC was formed into a layer having a thickness of 30 nm to serve as a hole-injecting layer on the ITO. Next, α-NPD was formed into a layer having a thickness of 15 nm to serve as a hole-transporting layer. Next, CBP serving as a host material for a light-emitting layer and Ir(ppy)$_3$ serving as a dopant were co-deposited from different deposition sources onto the hole-transporting layer to form a light-emitting layer having a thickness of 30 nm. The concentration of Ir(ppy)$_3$ was 10 wt %. Next, the compound 1 was formed into a layer having a thickness of 5 nm to serve as a hole-blocking layer on the light-emitting layer. Next, Alq$_3$ was formed into a layer having a thickness of 20 nm to serve as an electron-transporting layer. Further, LiF was formed into a layer having a thickness of 1.0 nm to serve as an electron-injecting layer on the electron-transporting layer. Finally, Al was formed into a layer having a thickness of 70 nm to serve as an electrode on the electron-injecting layer. The resultant organic EL device has such a layer construction that the electron-injecting layer is added between the cathode and the electron-transporting layer and the hole-blocking layer is added between the light-emitting layer and the electron-transporting layer in the organic EL device illustrated in FIG. 1.

An external power source was connected to the resultant organic EL device to apply a DC voltage to the device. As a result, it was confirmed that the device had such light-emitting characteristics as shown in Table 1. The columns "luminance", "voltage", and "luminous efficacy" in Table 1 show values (initial characteristics) at the time of driving at 20 mA/cm$^2$. The maximum wavelength of the emission spectrum of the device was 530 nm, and hence the acquisition of light emission from Ir(ppy)$_3$ was found.

Examples 4 to 9

Organic EL devices were each produced in the same manner as in Example 3 except that the compound 3, 10, 16, 17, 22, or 23 was used instead of the compound 1 as the hole-blocking material in Example 3.

Comparative Example 1

An organic EL device was produced in the same manner as in Example 3 except that the thickness of Alq$_3$ serving as the electron-transporting layer in Example 3 was changed to 25 nm and the hole-blocking layer was not formed.

Comparative Examples 2 to 5

Organic EL devices were each produced in the same manner as in Example 3 except that the compound H-1, H-2, H-3, or H-4 was used as the hole-blocking material in Example 3.

The organic EL devices obtained in Examples 3 to 9 and Comparative Examples 1 to 5 were evaluated in the same manner as in Example 3. As a result, it was confirmed that the devices had such light-emitting characteristics as shown in Table 1. It should be noted that the maximum wavelength of each of the emission spectra of the organic EL devices obtained in Examples 3 to 7 and Comparative Examples 1 to 5 was 530 nm, and hence the acquisition of light emission from Ir(ppy)$_3$ was identified. It should be noted that each of the host materials for the light-emitting layers used in Examples 3 to 9 and Comparative Examples 1 to 5 is CBP.

TABLE 1

|  | Hole-blocking material | Luminance (cd/m$^2$) | Voltage (V) | Visual luminous efficacy (lm/W) |
| --- | --- | --- | --- | --- |
| Example 3 | Compound 1 | 3,100 | 8.2 | 5.9 |
| Example 4 | Compound 3 | 3,400 | 7.9 | 6.8 |
| Example 5 | Compound 10 | 3,100 | 8.2 | 5.9 |
| Example 6 | Compound 16 | 3,000 | 8.2 | 5.7 |
| Example 7 | Compound 17 | 3,000 | 8.0 | 5.9 |
| Example 8 | Compound 22 | 3,200 | 8.4 | 6.0 |
| Example 9 | Compound 23 | 3,000 | 8.2 | 5.7 |
| Comparative Example 1 | — | 1,120 | 8.7 | 2.0 |
| Comparative Example 2 | H-1 | 1,300 | 7.5 | 2.7 |
| Comparative Example 3 | H-2 | 1,100 | 7.3 | 2.4 |
| Comparative Example 4 | H-3 | 1,500 | 7.2 | 3.3 |
| Comparative Example 5 | H-4 | 2,300 | 8.0 | 4.5 |

It is found from Table 1 that Examples 3 to 9 each using the ortho-carborane compound of the present invention in its hole-blocking layer show characteristics better than those of Comparative Example 1 not using the hole-blocking material and Comparative Examples 2, 3, 4, and 5 each using a compound other than that of the present invention.

INDUSTRIAL APPLICABILITY

The use of the ortho-carborane compound of the present invention as a host material having electron-transporting property for a light-emitting layer, a material for an electron-transporting layer, a material for a hole-blocking layer, or a material for an exciton-blocking layer, in an organic EL device can reduce the voltage at which the device is driven. In addition, the organic EL device using the material for phosphorescent devices has enabled the realization of an organic EL device improved in luminous efficacy, and having a long driving lifetime and high durability.

The invention claimed is:

1. A material for organic electroluminescent devices, comprising an ortho-carborane compound represented by the general formula (1):

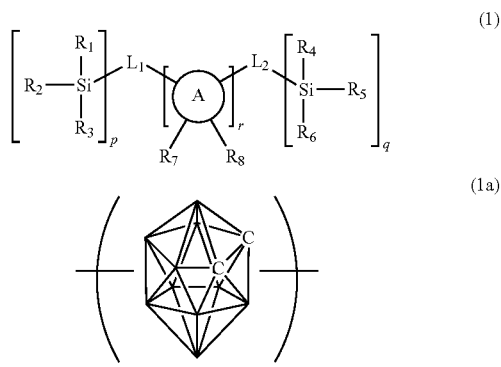

where ring A represents a divalent ortho-carborane group $C_2B_{10}H_{10}$ represented by the formula (1a), $L_1$ and $L_2$ each independently represent a substituted or unsubstituted aromatic hydrocarbon group having 6 to 30 carbon atoms, a substituted or unsubstituted aromatic heterocyclic group having 3 to 30 carbon atoms, or a linked aromatic group formed by linking 2 to 6 aromatic rings selected from the aromatic hydrocarbon group and the aromatic heterocyclic group, when $L_1$ or $L_2$ represents the linked aromatic group, the group may be linear or branched, and the aromatic rings to be linked may be identical to or different from each other, and $L_1$ represents a p+1-valent group and $L_2$ represents a q+1-valent group, $R_1$, $R_2$, $R_3$, $R_4$, $R_5$, and $R_6$ each independently represent an aliphatic hydrocarbon group having 1 to 12 carbon atoms, a substituted or unsubstituted aromatic hydrocarbon group having 6 to 18 carbon atoms, or a substituted or unsubstituted aromatic heterocyclic group having 3 to 17 carbon atoms, $R_7$ and $R_8$ each independently represent hydrogen, an aliphatic hydrocarbon group having 1 to 12 carbon atoms, a substituted or unsubstituted aromatic hydrocarbon group having 6 to 18 carbon atoms, or a substituted or unsubstituted aromatic heterocyclic group having 3 to 17 carbon atoms, p represents an integer of from 1 to 5, q represents an integer of from 0 to 5, and r represents an integer of from 1 to 4.

2. A material for organic electroluminescent devices according to claim 1, wherein the ortho-carborane compound represented by the general formula (1) comprises an ortho-carborane compound represented by the general formula (2):

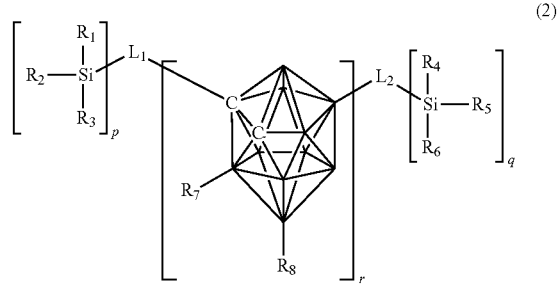

where $L_1$, $L_2$, $R_1$ to $R_8$, p, q, and r are identical in meaning to those in the general formula (1).

3. A material for organic electroluminescent devices according to claim 2, wherein in the general formula (2), $L_1$ and $L_2$ each independently represent a substituted or unsubstituted aromatic hydrocarbon group having 6 to 18 carbon atoms, a substituted or unsubstituted aromatic heterocyclic group having 3 to 17 carbon atoms, or a linked aromatic group formed by linking 2 to 6 aromatic rings selected from the aromatic hydrocarbon group and the aromatic heterocyclic group.

4. A material for organic electroluminescent devices according to claim 3, wherein in the general formula (2), $R_1$ to $R_6$ each independently represent an aliphatic hydrocarbon group having 1 to 10 carbon atoms, or an aromatic hydrocarbon group having 6 to 12 carbon atoms.

5. An organic electroluminescent device having a structure in which an anode, an organic layer, and a cathode are laminated on a substrate, wherein the organic layer comprises an organic layer containing the material for organic electroluminescent devices of claim 1.

6. An organic electroluminescent device according to claim 5, wherein the organic layer containing the material for organic electroluminescent devices comprises at least one layer selected from the group consisting of a light-emitting layer, an electron-transporting layer, a hole-blocking layer, and an exciton-blocking layer.

7. An organic electroluminescent device according to claim 5, wherein the organic layer containing the material for organic electroluminescent devices comprises an electron-transporting layer, a hole-blocking layer, or an exciton-blocking layer.

* * * * *